United States Patent [19]

Törnblom

[11] Patent Number: 4,767,986
[45] Date of Patent: Aug. 30, 1988

[54] OSCILLATING TRANSDUCERS FOR MONITORING THE SURFACE OF ELONGATED OBJECTS

[76] Inventor: Bengt H. Törnblom, Vikhus Rytterne, S-725 90 Västerås, Sweden

[21] Appl. No.: 933,903

[22] Filed: Nov. 24, 1986

[30] Foreign Application Priority Data

Nov. 25, 1985 [SE] Sweden ............................... 8505541

[51] Int. Cl.$^4$ .......................................... G01N 27/82
[52] U.S. Cl. ................... 324/227; 324/237; 324/241
[58] Field of Search ............... 324/207, 208, 225–227, 324/224, 234, 235–243, 260–262; 901/9, 46, 49

[56] References Cited

U.S. PATENT DOCUMENTS

| | | | |
|---|---|---|---|
| 3,906,357 | 9/1975 | Runshang | 324/227 X |
| 3,939,404 | 2/1976 | Tait | 324/238 X |
| 4,027,233 | 5/1977 | Shmakau et al. | 324/224 |
| 4,123,708 | 10/1978 | Vild et al. | 324/224 |
| 4,126,491 | 11/1978 | Karlsson | 324/238 X |
| 4,430,614 | 2/1984 | Gereg | 324/238 |
| 4,461,995 | 7/1984 | Harris | 324/224 |
| 4,476,434 | 10/1984 | Collins et al. | 324/233 |
| 4,604,574 | 8/1986 | Pasluszny et al. | 324/225 X |
| 4,644,274 | 2/1987 | Casarcia | 324/237 X |

Primary Examiner—Reinhard J. Eisenzopf
Assistant Examiner—Warren S. Edmonds
Attorney, Agent, or Firm—Watson, Cole et al.

[57] ABSTRACT

A device for measuring or testing of an object, for example rolled wire, a tube, or a billet, to detect surface discontinuities employs a sensing transducer which is oscillated backwards and forwards over the surface of the test object by means of a motor, the oscillations taking place in the form of a curved path extending transversely of the longitudinal extent of the object.

16 Claims, 3 Drawing Sheets

4,767,986

OSCILLATING TRANSDUCERS FOR MONITORING THE SURFACE OF ELONGATED OBJECTS

TECHNICAL FIELD

This invention relates to a device for monitoring elongated test objects (e.g. by scanning the surface thereof) to detect discontinuities such as blemishes, cracks, voids and distortions of cross-sectional shape. The invention has particular utility in monitoring the production of rolled material in a rolling mill for wire rod or the like.

DISCUSSION OF PRIOR ART

In the monitoring (e.g. measurement or testing) of elongated material, for example wire, rod or tubing of circular cross-section, rotary surface transducers are currently often used. In those cases where the material being monitored is hot (e.g. above 900° C.) and is moving at high velocity, as for example in the quality testing of rolled wire, it is necessary to use a large number of parallel-working transducers and to rotate each transducer very rapidly in order to reliably detect a surface crack. In the absence of high reliability of monitoring, a crack can otherwise be missed between the turns of the helically-formed scanning paths created by the rotating transducers.

One consequence of the high velocity and large number of transducers used in prior art monitoring is that it is difficult to transmit electrical signals between the transducers and the associated measuring electronics and that the equipment required to feed cooling medium (e.g. water) to each transducer (which is required in the case of monitoring high temperature material) is bulky and complicated.

OBJECTS OF THE INVENTION

One object of the present invention is to provide a solution to the problems mentioned above with regard to prior art monitoring equipment and other problems associated therewith.

A further object of the present invention is to provide an alternative to the above-described rotating surface transducers currently available.

A still further object is to provide monitoring equipment which is less expensive, bulky and sensitive to the environment than the prior art equipment.

A yet further object of the invention is to provide novel equipment for measuring and/or inspection, for example testing, of test objects with respect to a detectable property and which may be employed to advantage in connection with both rectilinear and curved surfaces of cold or hot materials.

A special object of the invention is to provide equipment for testing hot rolled wire or rod.

The invention, which is generally applicable, is well suited for use in connection with so-called eddy current testing and can be used on test objects such as, for example, a billet, a wire, a rod, a tube, a profiled section, or a sheet to monitor for some discontinuity such as a surface imperfection, a surface crack, the edge of a billet, a change in cross section, a void, the position of a crack or the depth of a crack.

SUMMARY OF THE INVENTION

According to the invention a device for monitoring a surface of a test object having a longitudinal extent for a discontinuity, which device comprises at least one transducer, and at least one drive means drivably connected to said at least one transducer, by means of which said at least one transducer is caused to move relative to a surface of the test object, is characterized in that the transducer movement oscillates along a curved path which is oriented substantially transversely to the longitudinal extent of the test object, and which substantially follows the surface of the test object at a suitable measuring distance therefrom.

The at least one transducer can be mounted in a crank-controlled bearing but other arrangements or components which can support and guide the path of the transducer(s) in a suitable manner relative to the surface of the test object, and in particular parallel to the surface, can also be used.

Inventions of a related kind are described in the specification of U.S. patent application No. 816,270 (filed on the 6th Jan. 1986 in the name of Bengt Törnblom) and in Swedish application No. 8503894-1. However, these earlier inventions do not possess the advantages provided by the present invention, especially in the case of monitoring test objects of circular cross-section moving with high velocity.

BRIEF DESCRIPTION OF THE DRAWINGS

The invention will now be described, by way of example, with reference to the accompanying schematic drawings, in which.

DESCRIPTION OF PREFERRED EMBODIMENTS

Figure 1:
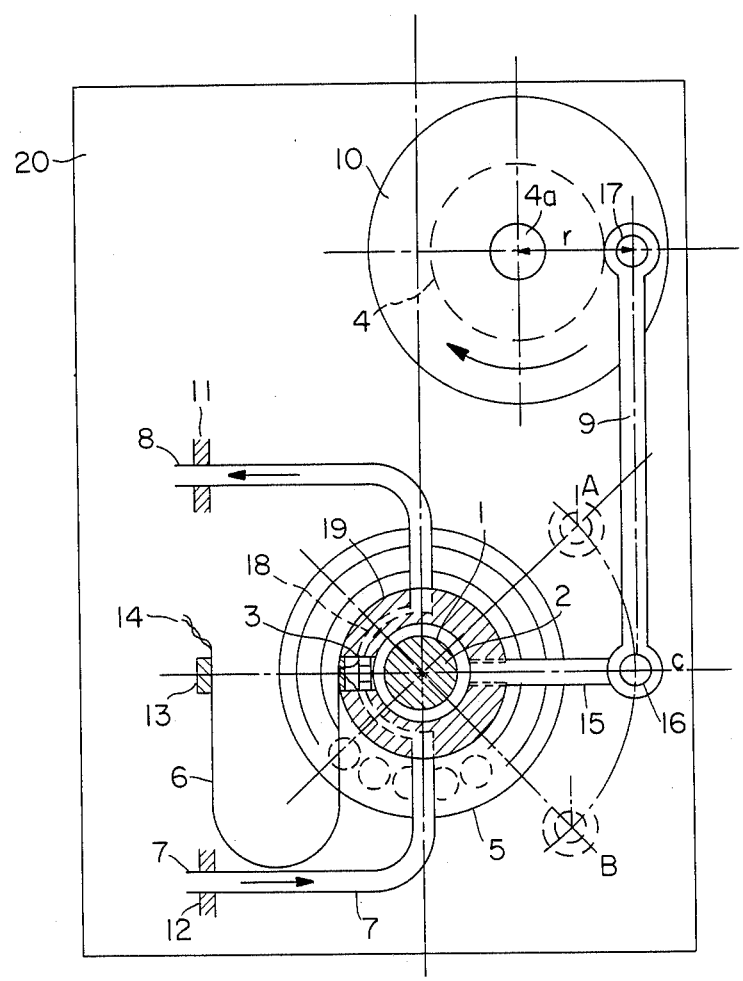
FIG. 1 is a partially sectional end view of a measuring device according to the invention with the test object extending out of the plane of the paper.

FIG. 1 shows a cross-section of the test object 1 which in this case, for example, consists of a hot cylindrical rod. The rod 1 contains a longitudinal surface crack 2, which, if possible, is to be detected by a transducer 3 when it passes over the crack 2. In a base plate or stand 20 of the device shown, a ball bearing 5 is mounted. In the inner ring of the ball bearing 5 a cylindrical body of revolution 19 is mounted. The body 19 is thus capable of rotating or oscillating because of its being journalled in the ball bearing 5. At least one surface transducer 3 is mounted in the body 19. The transducer 3 is cooled via coolant channels 18 which are connected to flexible conductors 7, 8 which, for example, consist of polyurethane hoses having good fatigue-resistant properties. Water is the preferred fluent cooling medium and can flow along the hoses 7, 8 in the direction shown by the arrows.

The transducer 3 is connected to an associated electronic unit (not shown) via a flexible electrical signal conductor 6 which, for example, consists of multi-pole electrical conductors or strips of metallic foil. Both the flexible cooling medium conductors 7, 8 and the flexible signal conductor 6 are shown anchored at one end to the base plate 20 via supports 11, 12, 13. These allow the body 19 to be rocked back and forth to a certain extent without the flexible conductors being destroyed. Due to the rocking motion, the transducer 3 will move at a substantially constant distance from the surface of the test object 1.

A motor 4 is mounted on the base plate 20. On the drive shaft 4a of the motor 4 a disk 10 is mounted, on which, in turn, a bearing journal 17 is eccentrically positioned. In similar manner, a bearing journal 16 is mounted on an arm 15 connected to the body 19. By linking the bearing journals 16, 17 with a crank arm 9, the body 19 will be made to oscillate (back and forth) transversely of the longitudinal extent of the test object 1 when the disk 10 is rotating. In FIG. 1 the rocking motion is illustrated by means of dashed positions A and B, which indicate the two extreme positions adopted by the bearing journal 16, the full line position C indicating the center position. The radial position of the bearing journal 17 on the motor disk 10 is adjusted to "r" so as to obtain a suitable oscillation amplitude A-B, suitably 90°.

In FIG. 1, only one surface transducer 3 is shown, which is to be understood as an extreme case. The invention is primarily intended for at least two transducers, since this makes the oscillation amplitude considerably easier to handle. In practice, the invention permits the use of a large number of transducers which are then suitably evenly distributed along the periphery of the test object. Four transducers is a useful number. With a plurality of transducers 3 the oscillation amplitude can be restricted in a simple manner, and this is of advantage in view of fatigue effects and the like. The larger the number of transducers, the smaller will be the oscillation amplitude required to cover the test object adequately and the faster the oscillation. Tests have shown that it is possible to work with oscillating frequencies greater than 50 Hz provided that the body 19 has a small mass. Especially in the case of larger oscillation amplitudes, for example ±45°, it is important for the flexible conductors (6, 7, 8) to be arranged in an optimum manner, for example so that they are exposed to minimum stress and are connected so as to be subjected to the smallest possible movement.

Figure 2:
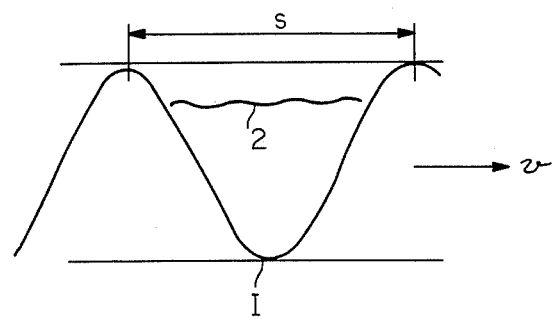
FIGS. 2, 3 and 4 show different trace patterns achieved with the monitoring transducer(s) of a device such as that shown in FIG. 1 over the surface of a test object.

In the case of a relative movement between the transducer arrangements and the test object, for example when the test object 1 moves at a velocity of v m/s, the oscillation will cause the respective transducer(s) to move in a path over the test object rather as shown in FIG. 2. This path is suitably referred to as a surface scanning pattern. In the worst case, the crack 2, which has a length of <S, may not be detected because it is not traversed by the scanning pattern if it is unfavourably located on the test object. In other words, in the worst case the largest crack which can escape detection has a length of S.

Figure 3:
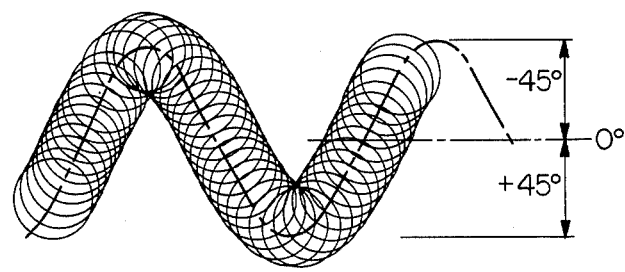

In FIG. 3 a scanning pattern is shown in which the transducer 3 has been rotated, whereby a rotation pattern is superposed on the oscillation pattern shown in FIG. 2. Also, in this case the fact that the oscillating velocity in the transverse direction becomes near zero at the peaks is less important, that is, the superposed rotation "takes over" if the tranvserve velocity is too small.

Figure 4:
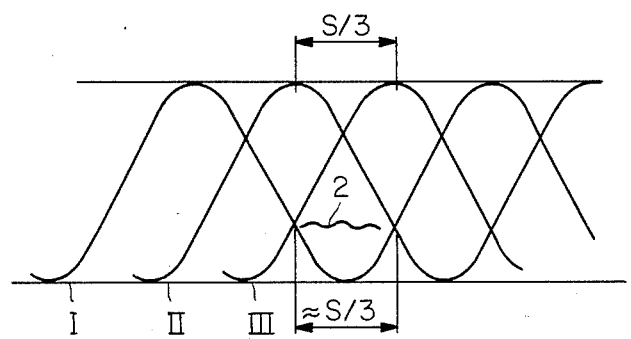

In order to improve this situation, a number "n" of transducers may be allowed to oscillate in such a way that their patterns form, relative to each other, "phase-displaced" patterns of a more fine-meshed nature. This, of course, permits the detection of shorter cracks. FIG. 4 shows such a pattern where n=3 and where the smallest detectable length of crack is approximately S/n, that is, S/3 in the worst case. This is a considerable improvement in relation to FIG. 2 or FIG. 3.

In practice, a more fine-meshed scanning pattern may be obtained, for example, by
(a) locating three oscillating bodies in succession along the test object 1, the distance between the transducers 3 being adjusted to the velocity of the object 1,
(b) oscillating the transducers 3 with mutually different phase positions,
(c) mounting the transducers 3 in the same body 19 but offset in phase in relation to each other, both in the peripheral direction and along the test object 1, and
(d) combinations of the above three steps.

Figure 5:
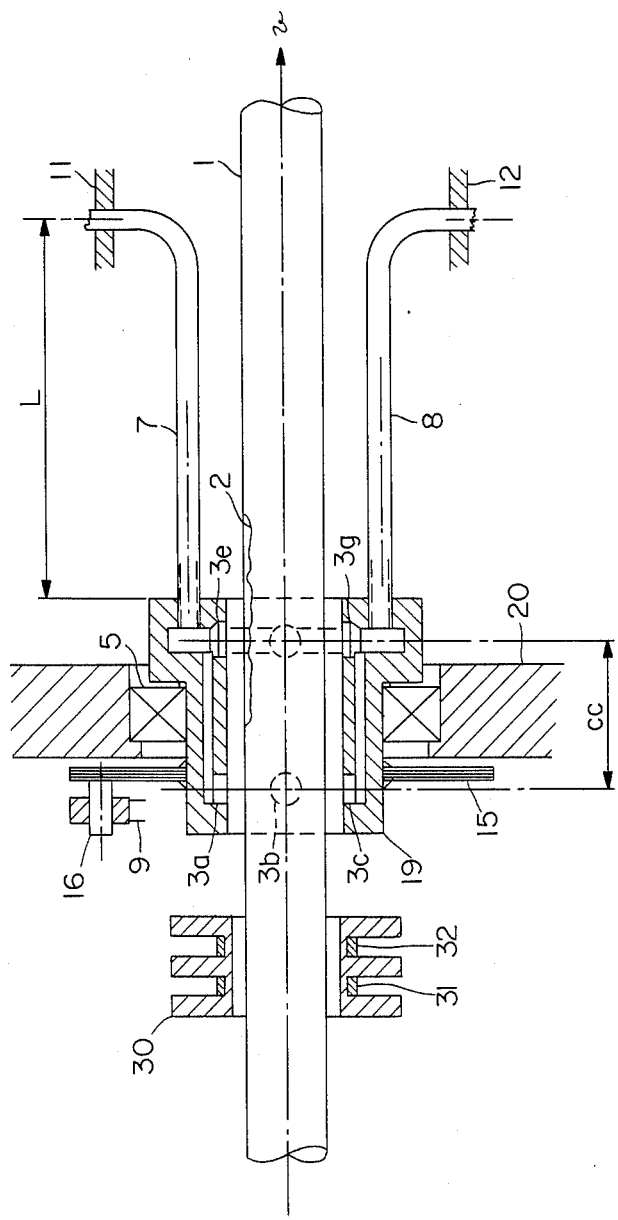
FIG. 5 shows, in side section, a further quality testing device according to the invention.

An attractive variant in practice is, for example to divide the cross-section of the test object into four quadrants and allow each one of four transducers to scan primarily its own quadrant periphery. To obtain a certain overlap, an oscillation amplitude of greater than 360/4 is chosen (i.e. a scan of rather more than ±45° for each transducer 3 is employed). In other words, a suitable basic arrangement may consist of four transducers spaced from each other by 90° along the periphery of the test object and each oscillating ≧±45°. Such an arrangement is shown in FIG. 5.

An oscillating frequency of 50 Hz corresponds to a period of 20 ms. If it is assumed that the test object consists of a rolled wire travelling with a velocity of 10 m/s, that is, 10 mm/ms (a commonly occurring velocity in this field of measurement) the length S in FIG. 2 will be $10_{mm/ms} \times 20_{ms} = 200$ mm. Thus, cracks shorter than 200 mm cannot be reliably detected.

It is, however, desirable to be able to detect cracks having a length of 100 mm at the velocity stated here. A relatively simple way of achieving this is to locate, as shown in FIG. 5, additional transducers ($3_{e-h}$), which are displaced relative to the first transducers ($3_{a-d}$) by a distance (cc) which is adapted to the current rolled wire velocity, that is, in the present case 10 mm/ms.

This method can, of course, be extended to theoretically comprise an almost infinite number of mutually displaced transducers, making the resulting scanning pattern very fine-meshed indeed.

The doubling of the number of transducers as shown in FIG. 5 implies that the smallest detectable length of crack is 200/2=100 mm, which is sufficient for most applications. In the case of crack lengths of >100 mm, ordinary annular transducers of a differential type often operate satisfactorily. This is the reason why the arrangement according to FIG. 5 is supplemented by an annular transducer 30 with associated differential windings, 31, 32, which theoretically enables the arrangement as a whole to detect the majority of cracks which might appear in practice.

The invention can be rendered more sophisticated by, for example, allowing the transducer 3 to be constituted by a probe which is allowed to rotate about a center axis perpendicular to the surface of the test object. This will cause the circular movement of the transducer probe to become superposed on the oscillating movement, whereby the scanning pattern becomes more extensive (as shown in FIG. 3) while at the same time the direction of movement of the transducer varies all the time. This results in any crack being almost invariably crossed during some scanning turn of the transducer.

In FIG. 5 the transducers $3_{a-d}$ are located at a distance cc in relation to the transducers $3_{e-h}$. By adapting the distance cc to the velocity of the rolled wire, combined patterns, for example according to FIG. 4, may be obtained. By arranging for the distance cc to be adjusted as the rolling speed changes, the transducer as a whole will be better adapted to monitor the production material. The same applies to transducer probes which in a practical case are often made adjustable in the vertical direction, again allowing the transducer(s) to be used over a large dimensional range.

FIG. 5 is also interesting in that the flexible conductors, for example the hoses 7, 8, are shown disposed to a significant extent parallel to the longitudinal direction of the test object and each has a length (L) which is large in relation to the oscillation amplitude. In this way, the flexing of the conductors per unit length is low and is evenly distributed which promises a long service life for these components. Numeral 15 in FIG. 5 designates a simple disk to which the crank arm 9 is connected via the journal 16.

The oscillating body 19 should, if possible, be made as small as circumstances permit to minimize the mechanical mass and the inertia, since this reduces the mechanical stresses imposed on the device during use.

It should be noted that most discontinuities/imperfections are successively rolled out in the rolling process so that, in the end, they will almost invariably have an orientation in the elongate direction of the test object, which consideration has been one of the starting-points in making the present invention.

In those cases where the test object is warm, ordinary water is a suitable cooling agent which is equally capable of cooling the mechanical parts and the transducer(s), without problems.

The degree figures stated in FIG. 3 refer to the oscillation amplitude, and therefore, for example, FIGS. 2, 3 and 4 may be regarded as scanning paths in the longitudinal direction of the rolled wire, in this case having a width of 90°.

In certain applications, for example during rolled wire testing, the ends of the rolled wire—and particularly the leading end—can easily be deformed and bent. This results in a tendency for the leading end to become wedged in the transducer, which in turn can destroy the transducer(s). Since in most cases it is desired to have a narrow transducer passage to afford high sensitivity in the monitoring, this may be a considerable problem. Because of the solutions provided by the present invention, for transmitting media such as air, water or oil, via flexible conductors, it is readily possible to transmit an operating medium, such as compressed air and to use such an operating medium, to vary the so-called "liftoff" of the transducer(s). Thus, when the leading end of the test object passes the transducer(s), the transducer(s) is/are moved so that the distance between the object and the transducer(s) is/are temporarily increased, thus avoiding the risk of damage of the transducer(s).

By providing the drive means with a heavy counterbalance wheel, vibrations caused by the oscillation can be suppressed. If it is desirable to improve the vibration suppression further, the arrangement according to FIG. 5 may, for example, be doubled and two bodies 19 be allowed to oscillate in opposition, that is, they oscillate in a direction opposite to each other, thus obtaining a balanced design.

The invention also embraces those cases where signal transmission takes place in some other manner than via the flexible conductors but where a medium of some kind is transmitted in accordance with the invention. The signal transmission may then, for example, be a contact-free inductive transmission whereas the cooling water is transmitted via hoses in the manner shown in FIG. 5.

As a consequence of the simplicity of transmitting signals, it is also possible to feed, in a simple manner, for example, electric current for feeding motors and the like mounted on the body 19. The motors may, for example, be used for rotating the transducer probes so as to obtain the rotational movement superposed on the oscillating movement shown in FIG. 3.

The invention also embraces those cases where, for example the crank device of FIG. 1 is replaced by an eccentric device or the like.

The present invention is primarily to be regarded as a device but it will be appreciated that a method of monitoring is also involved.

It should also be pointed out that the oscillating body 19 within the scope of the invention may consist of several sections, whereby the passage for the test object can be adapted to varying test object dimensions.

The present invention may, of course, be varied in many other ways within the scope of the following claims.

What is claimed is:

1. A device for monitoring the surface of an elongated test object for a discontinuity, comprising:
   at least two transducers with drive means drivably connected thereto, for causing said at least two transducers to move relative to said surface;
   said at least two transducers having different rotation centers and rotating in respective curved paths;
   said centers being displaced relative to each other in the longitudinal direction of said test object; and
   said respective curved paths at least partially covering the surface of said test object in longitudinally and laterally overlapping scanning paths.

2. A device according to claim 1, further comprising the transmission of at least one of electrical and cooling medium between said at least two transducers and a control means therefor via at least one flexible connecting means.

3. A device according to claim 2, in which the connecting means for electrical signals is a strip of metallic foil.

4. A device according to claim 2, in which the connecting means for cooling medium is a polyurethane hose.

5. A device according to claim 2, in which the at least one flexible connecting means is connected to said at least two transducers in a direction which substantially coincides with the longitudinal extent of the test object.

6. A device according to claim 1, in which said at least two transducers oscillate over the surface of the test object at a suitable distance therefrom with the aid of at least one guide means conforming to the cross-sectional shape of the test object.

7. A device according to claim 1, in which said at least two transducers are displaced, in relation to each other, in the direction of oscillation of the transducers.

8. A device according to claim 1, in which said at least two transducers are displaced, in relation to each other, in the direction of oscillation of the transducers.

9. A device according to claim 8, in which the relative angular displacement between the two transducers is 90°.

10. A device according to claim 6, in which said at least two transducers rotate in respective circular paths which are superimposed on the oscillating movement.

11. A device according to claim 1, in which said at least two transducers are cooled with a fluent cooling medium.

12. A device according to claim 1, in which the drive means comprises at least one motor with an associated eccentric device connected with said at least two transducers.

13. A device according to claim 12, in which the at least one motor is an electric motor and the eccentric device is a crank device.

14. A device according to claim 1, in which said at least two transducers, which at respective times, oscillate over different parts of the surface of the test object, the transducers being arranged in such a way in relation to the test object that their surface scanning patterns, in combination with movement of the test object in relation to the transducer arrangement, form patterns which permit monitoring of a discontinuity whose length in the direction of said longitudinal direction exceeds a certain limiting value.

15. A device according to claim 1, in which a fluent operating medium is transmitted to the oscillating transducers via flexible conductor and said flexible conductor is used for adjusting the distance of the transducers from the surface of the test object.

16. A device for monitoring the surface of an elongated test object for discontinuities, comprising:

at least two transducers with drive means drivably connected thereto, for causing said at least two transducers to move relative to the surface of said test object;

said at least two transducers having different rotation centers and rotating in respective curved paths;

said centers being displaced relative to each other in the longitudinal direction of said test object;

said paths at least partially covering the surface of said test object in longitudinally and laterally overlapping scanning paths; and said scanning paths comprising at least two surface scanning patterns obtained from different transducers, which patterns are a function of oscillation movements and the movements of said test object.

* * * * *